United States Patent [19]
Anderson

[11] Patent Number: 4,890,733
[45] Date of Patent: Jan. 2, 1990

[54] DISPOSAL RECEPTACLE FOR USED, SHARP, MEDICAL INSTRUMENTS OR OTHER BIOHAZARDS

[76] Inventor: Robert S. Anderson, 27213 N. Fairfield Rd., Wauconda, Ill. 60084

[21] Appl. No.: 162,614
[22] Filed: Mar. 1, 1988
[51] Int. Cl.⁴ .............................................. B65D 83/10
[52] U.S. Cl. ....................... 206/365; 206/366; 206/438; 220/1 T; 220/334; 220/335
[58] Field of Search ..................... 206/438, 365, 366; 220/1 T, 254, 334, 335; 232/44, 47

[56] References Cited

U.S. PATENT DOCUMENTS

| | | | |
|---|---|---|---|
| 1,044,306 | 11/1912 | Vertner | 220/1 T |
| 1,161,089 | 11/1915 | Waldo | 220/1 T |
| 3,306,486 | 2/1967 | Martino et al. | 220/1 T |
| 3,749,274 | 7/1973 | Mele et al. | 220/1 T |
| 4,032,037 | 6/1977 | Dubery et al. | 220/1 T |
| 4,176,610 | 12/1979 | Markham et al. | 232/44 |
| 4,351,434 | 9/1982 | Elisha | 206/366 |
| 4,363,417 | 12/1982 | Rhoades et al. | 220/1 T |
| 4,406,395 | 9/1983 | Scoggins | 220/1 T |
| 4,453,648 | 6/1984 | Harris et al. | 220/1 T |
| 4,520,926 | 6/1985 | Nelson | 206/366 |
| 4,580,688 | 4/1986 | Harris et al. | 206/365 |
| 4,662,516 | 5/1987 | Baker, Sr. et al. | 206/366 |
| 4,714,168 | 12/1987 | Johnson et al. | 206/366 |
| 4,715,498 | 12/1987 | Hanifl | 206/366 |
| 4,722,472 | 2/1988 | Bruno | 206/366 |
| 4,736,860 | 4/1988 | Bemis | 220/1 T |

FOREIGN PATENT DOCUMENTS

| | | | |
|---|---|---|---|
| 756371 | 4/1967 | Canada | 232/44 |
| 103484 | 1/1966 | Denmark | 232/44 |
| 31372 | 9/1960 | Finland | 220/1 T |

*Primary Examiner*—David T. Fidei

[57] ABSTRACT

A receptacle for disposal of used, sharp, medical instruments or other biohazards, comprising an upright container, which is closed except for a slot in a top wall, a chute which is mounted integrally to the top wall so as to extend downwardly, a shroud, which is mounted integrally to the top wall so as to extend upwardly, and a scoop, which is mounted pivotally to the top wall at a back margin of the slot. The scoop and shroud are configured so as to form a tray, which is adapted to hold one or more such instruments until the instruments held by the tray are discharged through the slot, via the chute, into the container. The scoop, shroud, and chute are configured so as to impede an object, such as a person's finger, which may have been inserted through the slot from reaching any such instruments in the containers. The scoop and chute are configured so as to impede any liquid contents of the container from splattering outside the receptacle.

7 Claims, 2 Drawing Sheets

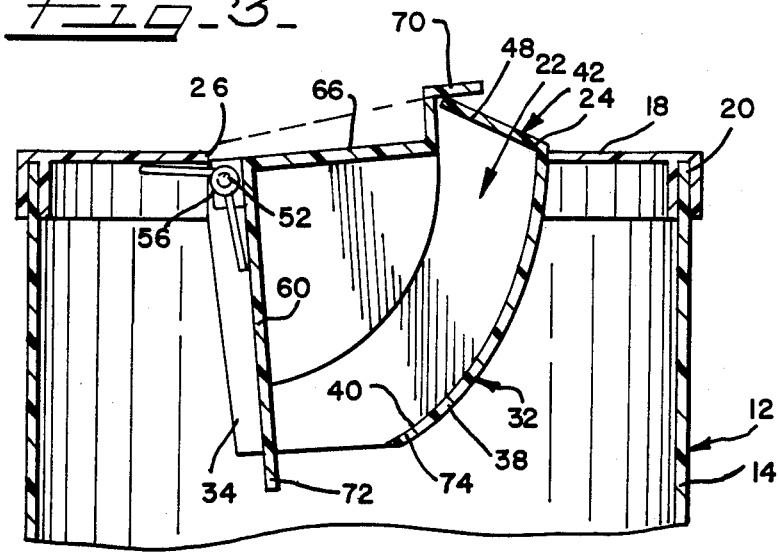
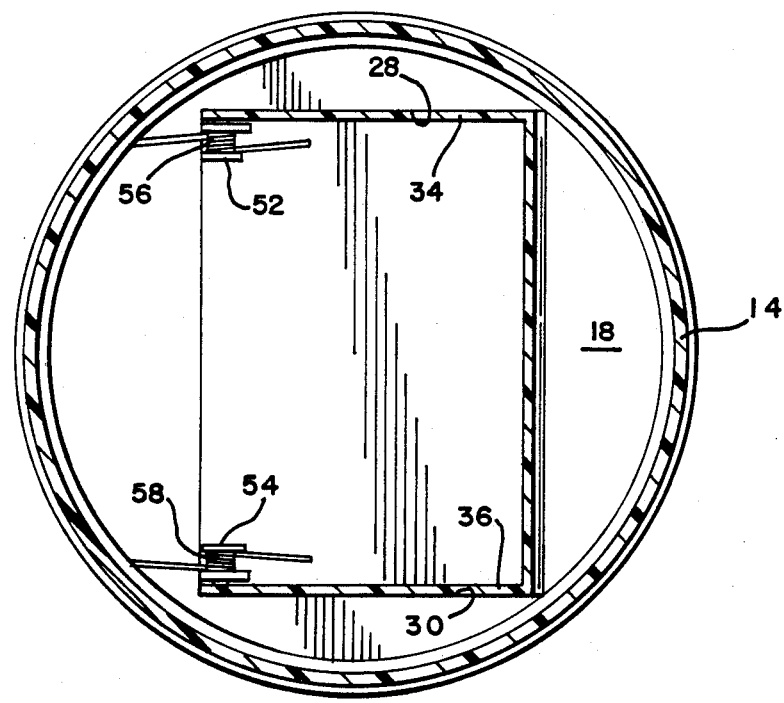

DISPOSAL RECEPTACLE FOR USED, SHARP, MEDICAL INSTRUMENTS OR OTHER BIOHAZARDS

FIELD OF THE INVENTION

This invention pertains to improvements in receptacles for disposal of used, sharp, medical instruments, such as scalpels and hypodermic syringes and needles, or other biohazards.

BACKGROUND OF THE INVENTION

In efforts to minimize risks of infection and to minimize abuse of injectable drugs, disposal receptacles for used, sharp, medical instruments, so-called "sharps", such as scalpels and hypodermic syringes and needles, have come into widespread use in hospitals, medical clinics, physicians' offices, and other settings where such instruments are used. Similar receptacles are used also to dispose of other biohazards.

Typically, such a receptacle comprises a closed container, into which such instruments are deposited through a slot or another form of portal providing restricted access to the container, and the receptacle has some means to impede a person attempting to insert his or her fingers from reaching any such instruments that have been deposited into the receptacle, to impede any liquid contents from splattering onto anything outside the receptacle, or to effect both purposes.

Some known types of receptacles for disposal of such items are exemplified in Meseke et al. U.S. Pat. No. 4,121,755, Smith U.S. Pat. No. 4,315,592, Simpson U.S. Pat. No. 4,410,086, Pepper U.S. Pat. 4,488,643, Harris et al. U.S. Pat. No. 4,580,688, and Kirskey U.S. Pat. No. 4,576,281.

In view of growing concerns over risks of infection with hepatitis, acquired immune deficiency syndrome, and other infectious diseases, and over abuse of injectable drugs, there has been a need, to which this invention is addressed, for improvements in receptacles for disposal of used, sharp, medical instruments or other biohazards.

SUMMARY OF THE INVENTION

This invention pertains to a receptacle, in an improved form, for disposal of used, sharp, medical instruments, such as scalpels and hypodermic syringes and needles. A disposal receptacle according to this invention may be also used to dispose of other biohazards.

Broadly, a receptacle according to this invention comprises an upright container, which is closed except for a slot in a top wall of the container, a chute, which is mounted integrally to the top wall, a shroud, which also is mounted integrally to the top wall, and a scoop, which is mounted pivotally to the top wall at a back margin of the slot for pivotal movement between an article-receiving position wherein the scoop closes the slot and a discharge position wherein any such instruments that have been placed in the scoop are discharged through the slot, via the chute, into the container.

As explained below, the scoop and shroud form a tray, which is adapted to hold one or more such instruments until the instruments held by the tray are discharged into the container. The scoop, shroud, and chute cooperate to impede an object, such as a person's finger, which may have been inserted through the slot from reaching any such instruments that have been discharged into the container. The scoop and chute impede any liquid contents of the container from splattering onto anything outside the receptacle.

Specifically, the chute includes a pair of side panels, which respectively extend downwardly from the side margins of the slot, and a front panel, which extends downwardly from the front margin of the slot. Likewise, the shroud includes a pair of side panels, which respectively extend upwardly from the side margins of the slot, and a front panel, which extends upwardly from the front margin of the slot. Moreover, the scoop includes a floor panel, which is disposed horizontally and adapted to close the slot when the scoop is pivoted to the article-receiving position, a pair of side panels, which extend upwardly from the floor panel when the scoop is pivoted to the article-receiving position, and which fit between the side panels of the shroud and between the side panels of the chute, and a back or cover panel, which extends upwardly when the scoop is pivoted to the article-receiving position.

Accordingly, the respective panels of the scoop and shroud form the tray noted above. Likewise, the respective panels of the scoop, shroud, and chute impede an article, such as a person's finger, which may have been inserted through the slot while the container remains upright from reaching any such instruments that have been discharged into the container. Moreover, the respective panels of the scoop and chute impede any liquid contents of the container from splattering onto anything outside the receptacle.

A front panel of the chute curves downwardly and backwardly so as to have a generally curvilinear surface. Thus, the front edge of the floor panel of the scoop remains adjacent to such a generally curvilinear surface when the scoop is being pivoted between its positions. The lower edge of the front panel of the chute is spaced from the front edge of the floor panel of the scoop when the scoop has been pivoted to the discharging position so as to allow any instruments in the scoop to drop from the scoop into the container.

The front panel of the shroud extends upwardly and backwardly so as to overlie a front portion of the slot, and so as to restrict pivotal movement of the scoop and define the limits of the article-receiving position. The back or cover panel of the scoop has an upper lip, which engages the front panel of the shroud so as to define the limits of the pivotal movement of the scoop to the discharge position. In this discharge position, as shown in FIG. 3, the scoop and the shroud interact to close the slot.

The receptacle may further comprise means for biasing the scoop to the article-receiving position. Such means may comprise, as an example, a pair of torsion springs. Alternatively, the scoop may be biased by its own weight to the discharge position.

Numerous other advantages and features of the present invention will become readily apparent from the following detailed description of the invention and the embodiments thereof, from the claims, and from the accompanying drawings in which the details of the invention are fully and completely disclosed as a part of this specification.

BRIEF DESCRIPTION OF THE DRAWING

FIG. 3 is a fragmentary, sectional view, as taken on a diametrical plane through an upper portion of the receptacle, showing the receptacle with the scoop in a discharge position; and FIG. 4 is a cross-sectional view, as taken along line 4—4 of FIG. 2, in a direction indicated by arrows.

DETAILED DESCRIPTION OF PREFERRED EMBODIMENTS

Figure 1:
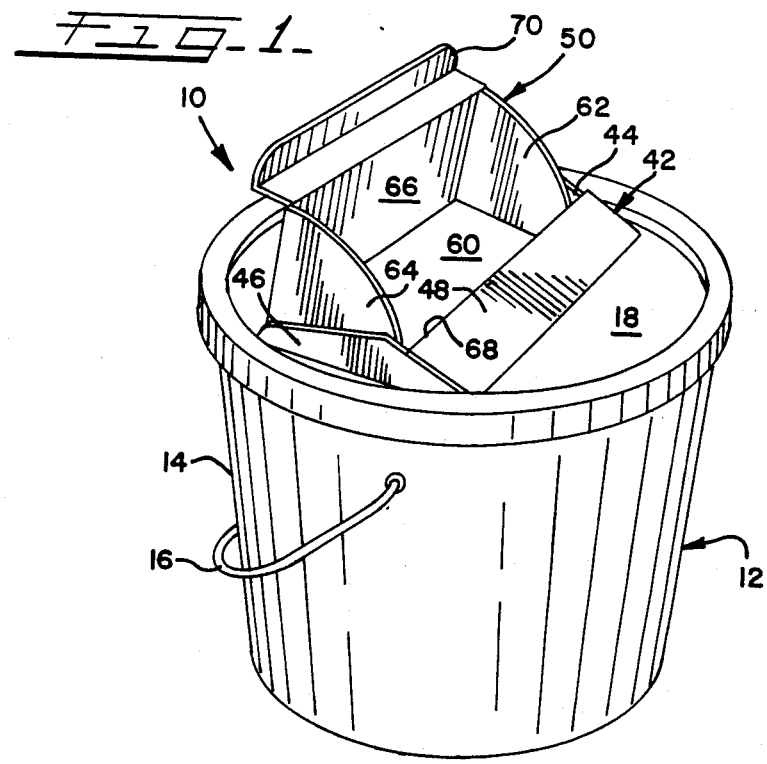
FIG. 1 is a perspective view of one embodiment of a receptacle for disposal of used, sharp, medical instruments or other biohazards, incorporating the present invention.

While this invention is susceptible of embodiment in many different forms, there is shown in the drawings and will be described herein in detail a specific embodiment thereof with the understanding that the present disclosure is to be considered as an exemplification of the principles of the invention and is not intended to limit the invention to the specific embodiment illustrated.

As shown in the drawings, a receptacle 10 is provided for disposal of used, sharp, medical instruments, such as scalpels and hypodermic syringes and needles, or other biohazards.

The receptacle 10 comprises an upright container 12, in the form of a pail or bucket 14 having a bail 16, and a cover 18 providing a top wall for the container 12. The cover 18 is welded, bonded by a suitable adhesive, or otherwise locked to the pail 14 around an upper edge 20 of the pail 14. The container 12 is closed except for a slot 22 in the cover 18. The slot 22, which is generally rectangular, has a front margin 24, a back margin 26, and side margins 28, 30.

Figure 2:
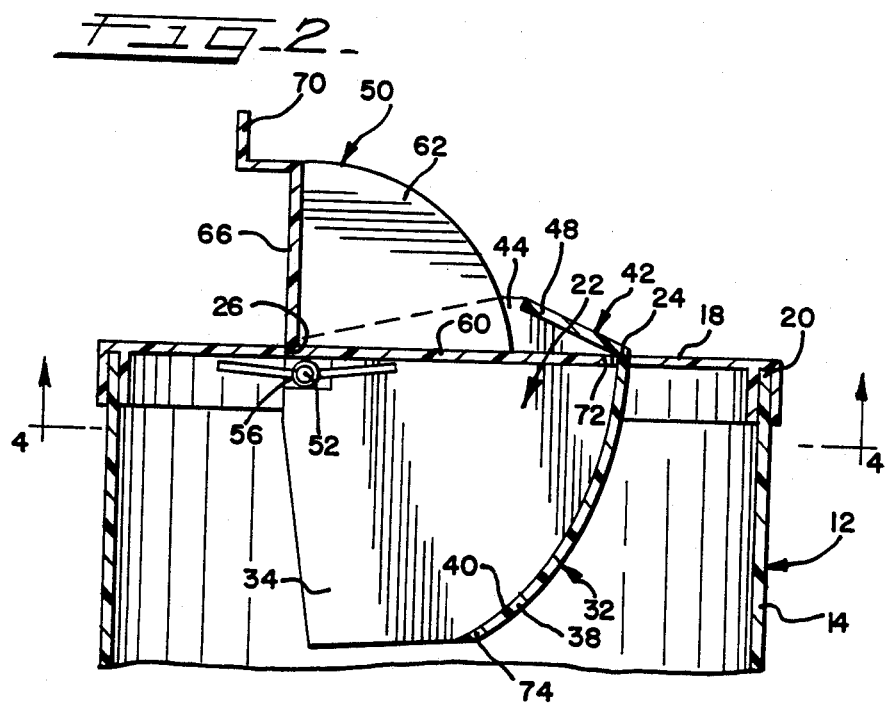
FIG. 2 is a fragmentary, sectional view, as taken on a diametrical plane through an upper portion of the receptacle shown in FIG. 1, showing the receptacle with the scoop in an article-receiving position.

A chute 32 is mounted integrally to the cover 18 so as to extend downwardly from the cover 18 into the container 12. The chute 32 includes a pair of side panels 34, 36, which respectively extend downwardly into the container 12 from the side margins 28, 30, of the slot 22. The chute 32 also includes a front panel 38, which is generally rectilinear in plan view, and but which is curved as it extends downwardly and backwardly from the front margin 24 of the slot 22 into the container 12 so as to have a generally curved surface 40 facing backwardly and upwardly, as shown in FIGS. 2 and 3.

A shroud 42 is mounted integrally to the cover 18 so as to extend upwardly from the cover 18. The shroud 42 includes a pair of side panels 44, 46, which respectively extend upwardly from the side margins 28, 30, of the slot 22. The shroud 42 also includes a front panel 48, which extends upwardly and backwardly from the front margin 24 of the slot 22 so as to overlie a front portion of the slot 22.

A scoop 50 is mounted pivotally to the cover 18 at the back margin 26 of the slot 22 by means of pivot pins 52, 54, mounted respectively to the side panels 34, 36, of the chute 32. A pair of torsion springs 56, 58, which are respectively piloted around the pivot pins 52, 54, may be used if it is desired to bias the scoop 50 to an article-receiving position as shown in FIGS. 1 and 2. The scoop 50 can be manually pivoted to a discharge position, such as shown in FIGS. 3 and 4. In this position, any such instruments that have been placed into the scoop 50 are discharged via the chute 32 into the container 12 through the gap between the scoop the 50 and the chute 32. The scoop 50 closes the slot 22 in both the article-receiving position shown in FIG. 2, and in the article-discharge position shown in FIG. 3. In an alternative construction, the springs 56, 58, are omitted, and the scoop 50 is biased by its own weight to the discharge position.

The scoop 50 includes a floor panel 60, which is disposed horizontally and adapted to close the slot 22 when the scoop 50 is pivoted to the article-receiving position. The floor panel 60 engages the front panel 48 of the shroud 42, as shown in FIG. 2, upon pivotal movement of the scoop 50 to the article-receiving position. The front panel 48 extends upwardly and backwardly, as mentioned above, and thus acts as a stop to limit pivotal movement of the scoop 50 to the article-receiving position.

The scoop 50 also includes a pair of side panels 62, 64, which are transverse to the floor panel 60 and which fit between the side panels 44, 46, of the shroud 42 and between the side panels 34, 36, of the chute 32. The scoop 50 also includes a back or cover panel 66, formed integrally therewith and which is disposed at an angle thereto. The back or cover panel 66 extends upwardly from the rear edge of the floor panel 60 when the scoop 50 is pivoted to the article-receiving position, and The cover panel 66 engages an upper edge 68 of the front panel 48 of the shroud 42 to close the slot 22 when the scoop 50 is pivoted to the discharging position. Thus, the upwardly and backwardly extending shroud front panel 48 the scoop 50 to the discharging position. The back panel 66 has an upper lip or handle 70 which is offset therefrom and 70, which extends beyond the front panel 48 when the scoop 50 is pivoted to the discharge position, and which thus facilitates manipulation of the scoop 50. The upper lip 70 engages the front panel 48 so as to limit pivotal movement of the scoop 50 to the discharge position.

The floor panel 60 of the scoop 50 has a front edge 72, which traverses a path adjacent to the generally curved surface 40 of the front panel 38 of the chute 32 when the chute 50 is being pivoted from the article-receiving position toward the discharge position. The front panel 38 of the chute 32 has a lower edge 74, which terminates at a point spaced from the front edge 72 of the floor panel 60 when the scoop 50 has been pivoted to the discharge position. Any instruments in the scoop 50 are thus discharged from by the scoop 50 and drop between the spaced edges 72, 74, when the scoop 50 is pivoted to the discharge position.

The respective panels of the scoop 50 and the respective panels of the shroud 42 are configured and cooperate so as to form a tray, which is adapted to hold one or more such instruments until the instruments held by the tray are discharged into the container 12.

The respective panels of the scoop 50, the respective panels of the shroud 42, and the respective panels of the chute 32 are also configured and cooperate so as to impede and substantially preclude an object, such as a person's finger, which may have been inserted through the slot 22 while the container remains upright from reaching any such instruments that have been discharged into the container 12. Means (not shown) may be also provided to secure the container 12 in an upright orientation.

The respective panels of the scoop 50 and the respective panels of the chute 32 are further configured and cooperate so as to impede any liquid contents of the container 12 from splattering onto anything outside the receptacle 10.

Except for the bail 16, which may be made of steel wire, the receptacle 10 may be advantageously made of polymeric components.

From the foregoing, it will be observed that numerous variations and modifications may be effected without departing from the true spirit and scope of the novel concept of the invention. It is to be understood that no limitation with respect to the specific apparatus illustrated herein is intended or should be inferred. It is, of course, intended to cover by the appended claims all such modifications as fall within the scope of the claims.

I claim:

1. A receptacle for disposal of used, sharp, medical instruments, or other biohazards, comprising:
   an upright container including a top wall provided with a slot having front, back, and side margins, said container being closed, except for said slot;
   chute means mounted integrally to said top wall, said chute means including side panel means depending from the side margins of said slot into said container, and front panel means depending from the front margin of the slot into said container;
   shroud means affixed to the top wall, said shroud means including side panel means extending upwardly from the side margins of said slot, and front panel means extending upwardly and backwardly from the front margin of said slot to overlie a portion thereof; and
   scoop means mounted pivotally to said top wall at the back margin of the slot for pivotal movement between a first position for receiving instruments deposited therein, and a second position for discharging instruments therefrom into said container;
   said scoop means including generally planar floor panel means, generally planar back panel means formed integrally with said floor panel means and disposed at an angle thereto and extending therefrom a point adjacent to said pivotal mounting of said scoop to said top wall, and a pair of side panel means extending between and connected to said floor panel means and said cover panel means; said scoop side panel means fitting closely adjacent to and between said shroud side panel means and said chute side panel means;
   the respective panel means of said scoop means and said shroud means cooperating to define tray means for receiving and holding one or more of such deposited instruments prior to discharge thereof into said container and interacting to impede an object from extending through the slot into the container and from reaching any instruments disposed within said container and any liquid contents within the container from splattering outside thereof.

2. A receptacle as claimed in claim 1, wherein:
   the forward edge of said scoop floor panel means and the edge of said scoop cover panel means are engageable with said shroud front panel means to define the limits of said pivotal movement of said scoop means between the article-receiving and discharge positions, respectively.

3. A receptacle as claimed in claim 1, wherein:
   said front panel means of said chute means curves downwardly and backwardly to define a generally curvilinear surface; and
   the front edge of said scoop floor panel means traverses a path closely adjacent to the generally curvilinear surface of said chute front panel means when said scoop means is pivoted between the article-receiving and the discharge positions thereof, said front edge of said scoop floor panel means being spaced from the lower edge of the chute curvilinear front panel means when said scoop means is in the discharge position for allowing instruments to pass therebetween and discharge into said container.

4. A receptacle as claimed in claim 3, wherein:
   said front edge of said scoop floor panel means engages said shroud front panel means to limit said pivotal movement of said scoop means toward the article-receiving position.

5. A receptacle as claimed in claim 4, wherein:
   said scoop cover panel means engages with said shroud front panel means to limit said pivotal movement of said scoop means toward the discharge position.

6. A receptacle as claimed in claim 1, wherein:
   the edge of the cover panel means of said scoop means remote from said floor panel means includes a lip portion offset from said cover panel means, said lip portion being engageable with the said front panel of said shroud means to define the limits of the pivotal movement of said scoop means towards said discharge position.

7. A receptacle as claimed in claim 3, including: means for biasing said scoop means to said article-receiving position.

* * * * *